United States Patent
Fuchs

(10) Patent No.: US 6,784,311 B2
(45) Date of Patent: Aug. 31, 2004

(54) METHOD OF PRODUCING 3-AMINOALKANOIC ACID ESTERS

(75) Inventor: Rudolf Fuchs, Sion (CH)

(73) Assignee: Lonza AG, Basel (CH)

( * ) Notice: Subject to any disclaimer, the term of this patent is extended or adjusted under 35 U.S.C. 154(b) by 1 day.

(21) Appl. No.: 10/204,461

(22) PCT Filed: Feb. 21, 2001

(86) PCT No.: PCT/EP01/01955
§ 371 (c)(1),
(2), (4) Date: Aug. 21, 2000

(87) PCT Pub. No.: WO01/62707
PCT Pub. Date: Aug. 30, 2001

(65) Prior Publication Data
US 2003/0114704 A1 Jun. 19, 2003

Related U.S. Application Data

(60) Provisional application No. 60/203,902, filed on May 12, 2000.

(30) Foreign Application Priority Data

Feb. 22, 2000 (EP) ............................................ 00103714

(51) Int. Cl.[7] ............................................ C07C 229/00
(52) U.S. Cl. ........................... 560/155; 560/37; 560/38; 560/168; 564/442; 546/335; 562/553
(58) Field of Search ............................ 560/155, 37, 38, 560/168; 564/442; 546/335; 562/553

(56) References Cited

FOREIGN PATENT DOCUMENTS

| EP | 0144980 | | 6/1985 |
|---|---|---|---|
| RU | 2026289 C1 | | 9/1995 |
| RU | 2026289 | * | 9/1995 |

OTHER PUBLICATIONS

Bartoli, Giuseppe, et al., "Chemo–and Diastereoselective Reduction of beta–Enamino Ester: A Convenient Synthesis of Both cis– and trans–gamma–Amino Esters", J.Org. Chem., vol. 50, No. 18, 1994, pp. 5328–5335.

Database Chemans 'Online!' Chemical Abstracts Service, Columbus, Ohio, U.S., Murzagulova, K.B., et al.: "Commercial Method for Production of 2,5–dimethyl–4–piperidone".

Murzagulova, K.B., et al., Pharmaceutical Chemistry Journal, vol. 32, No. 9, (1998), 507–508.

Database WP1, Section Ch, Week 199532, Derwent Publication Ltd., London, GB, An1995–244725, XP002171635.

* cited by examiner

*Primary Examiner*—Paul J. Killos
*Assistant Examiner*—Hector M Reyes
(74) *Attorney, Agent, or Firm*—Fisher, Christen & Sabol

(57) ABSTRACT

Process for the preparation of 3-aminoalkanoic acid esters of the general formula:

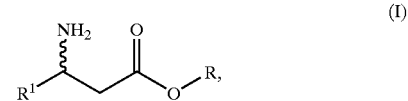

in which R is $C_{1-6}$-alkyl and $R^1$ is hydrogen, $C_{1-6}$-alkyl or phenyl, or their salts, by catalytic hydrogenation of the corresponding 3-amino-2-alkenoic acid esters of the general formula:

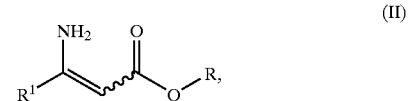

in which R and $R^1$ have the above mentioned meanings. The hydrogenation is carried out in the presence of a strong acid and the salt of the 3-aminoalkanoic acid ester (I) and the strong acid formed is optionally converted into the free 3-aminoalkanoic acid ester (I) or into another salt in a manner known per se.

21 Claims, No Drawings

METHOD OF PRODUCING 3-AMINOALKANOIC ACID ESTERS

This application claims the benefit of provisional application No. 60/203,902 filed May 12, 2000.

The invention relates to a process for the preparation of 3-aminoalkanoic acid esters from 3-amino-2-alkenoic acid esters.

Several processes for the hydrogenation of 3-amino-2-alkenoic acid esters are known.

RU-C-2 026 289 describes the hydrogenation of ethyl 3-aminocrotonate in the presence of a nickel catalyst.

U.S. Pat. No. 4,585,887 describes the preparation of optically active 3-aminoalkanoic acid esters, a β-ketoester being reacted with a chiral amine and the enamine resulting therefrom being hydrogenated in the presence of a Pt/C catalyst.

The hydrogenation rate and the selectivity are not satisfactory in the abovementioned, known hydrogenation processes.

The object of the present invention was to make available a process for the preparation of 3-aminoalkanoic acid esters from 3-amino-2-alkenoic acid esters, the hydrogenation proceeding rapidly and with high selectivity.

According to the invention, this object is achieved by the process according to Claim 1.

It has now been found that catalytic hydrogenation proceeds very rapidly in the presence of a strong acid and 3-aminoalkanoic acid esters are obtained in high yield.

The process according to the invention relates to the preparation of 3-aminoalkanoic acid esters of the general formula

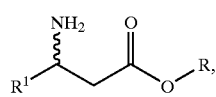

(I)

in which R is $C_{1-6}$-alkyl and $R^1$ is hydrogen, $C_{1-6}$-alkyl or phenyl, or their salts, by catalytic hydrogenation of the corresponding 3-amino-2-alkenoic acid esters of the general formula

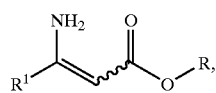

(II)

in which R and $R^1$ have the abovementioned meanings.

The process is characterized in that the catalytic hydrogenation is carried out in the presence of a strong acid and the salt of the 3-aminoalkanoic acid ester (I) and the strong acid formed is optionally converted into the free 3-aminoalkanoic acid ester (I) or into another salt in a manner known per se.

$C_{1-6}$-alkyl is understood here and below as meaning all linear or branched alkyl groups having 1–6 carbon atoms, such as, for example, methyl, ethyl, propyl, isopropyl, butyl, isobutyl, sec-butyl, tert-butyl, pentyl, isopentyl, tert-pentyl, neopentyl, hexyl or isohexyl.

The radical R is preferably methyl.

Strong acids here and below are in particular understood as meaning hydrohalic acids, such as, for example, hydrochloric or hydrobromic acid, sulfuric acid, sulfonic acids, such as, for example, methanesulfonic, benzenesulfonic or p-toluenesulfonic acid, and perfluoro-alkanoic acids.

The strong acid is expediently employed in an equimolar amount or in a small excess, based on the ester.

A preferred hydrohalic acid is hydrochloric acid.

Suitable sulfonic acids are, for example, methanesulfonic acid or p-toluenesulfonic acid.

Trifluoroacetic acid is a preferred perfluoro-alkanoic acid.

Suitable catalysts are, in particular, platinum, palladium or rhodium catalysts, in particular supported catalysts. A platinum supported catalyst is particularly preferred.

Suitable support materials are all customary support materials such as, for example, activated carbon, alumina, silica, silicon aluminum oxide, silicon carbide, titania, magnesia or zeolites. Activated carbon is preferred.

The supported catalysts contain expediently approximately 1–30% by weight, preferably approximately 5–10% by weight, of noble metal.

Catalysts of this type are commercially obtainable, e.g. from Degussa or Heraeus.

The hydrogenation is expediently carried out in an anhydrous solvent.

Suitable solvents are in particular those from the group of the lower alcohols (e.g. methanol, ethanol), esters (e.g. methyl acetate), ethers (e.g. tetrahydrofuran, dioxane, diethyl ether) or haloalkanes (e.g. dichloro-methane, 1,2-dichloroethane). Anhydrous methanol is especially preferred.

The hydrogenation is expediently carried out at temperatures of 0–150° C. and pressures of 1–100 bar, preferably at room temperature (20–30° C.) and pressures of 5–10 bar.

The 3-amino-2-alkenoic acid esters (II) can be obtained by reaction of ammonia with 3-oxoalkanoic acid esters, as described in the abovementioned Russian patent publication.

A further possibility for the preparation of 3-amino-2-alkenoic acid esters (II) is the ring-opening of β-lactams described in DE-A-24 25 705 and subsequent esterification by reaction with alcohol/HCl.

The methanesulfonates of the 3-ammonioalkanoic acid esters of the general formula

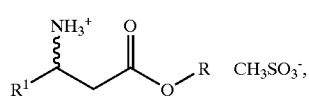

(I')

in which R and $R^1$ have the abovementioned meanings, are novel and likewise a subject of the invention.

The conversion of the salt of the 3-aminoalkanoic acid ester (I) and the strong acid into the free 3-aminoalkanoic acid ester (I) can be carried out in a manner known per se, for example by addition of sodium hydroxide solution.

The following examples illustrate the implementation of the process according to the invention, without a restriction being seen therein.

EXAMPLE 1

Preparation of Methyl (RS)-3-Aminobutyrate Hydrochloride (In the Presence of Hydrochloric Acid)

5.0 g (43.4 mmol) of methyl 3-aminocrotonate, 70 ml of a 9.3% strength solution of 17 g (43 mmol) of HCl gas in anhydrous methanol and 0.22 g of Pt/C catalyst (Heraeus K0129) were introduced into a 160 ml Parr autoclave. The hydrogenation was carried out for 3 hours at 21–25° C. under 5–10 bar of hydrogen. The catalyst was then filtered off and the solvent was completely removed by distillation on a rotary evaporator. 6.34 g of pure methyl (RS)-3-aminobutyrate hydrochloride were obtained as an oil.

EXAMPLE 2
Preparation of Methyl (RS)-3-Aminobutyrate Sulfate or Hydrogen Sulfate (In the Presence of Sulfuric Acid)

5.0 g (43.4 mmol) of methyl 3-aminocrotonate, 70 ml of anhydrous methanol, 1.5 equivalent of sulfuric acid and 0.22 g of Pt/C catalyst (Heraeus K0129) were introduced into a 160 ml Parr autoclave. The hydrogenation was carried out for 2 hours at approximately 25° C. under 3–10 bar of hydrogen. The catalyst was then filtered off and the solvent was completely removed by distillation on a rotary evaporator. 6.13 g of pure methyl (RS)-3-aminobutyrate sulfate were obtained as an oil. The hydrogensulfate can be prepared correspondingly.

EXAMPLE 3
Preparation of Methyl (RS)-3-Aminobutyrate Methanesulfonate (In the Presence of Methanesulfonic Acid)

5.0 g (43.4 mmol) of methyl 3-aminocrotonate, 70 ml of anhydrous methanol, 1.0 equivalent of methanesulfonic acid and 0.22 g of Pt/C catalyst (Heraeus K0129) were introduced into a 160 ml Parr autoclave. The hydrogenation was carried out for 2 hours at approximately 20° C. under 5–10 bar of hydrogen. The catalyst was then filtered off and the solvent was completely removed by distillation on a rotary evaporator. 6.2 g of pure methyl (RS)-3-aminobutyrate methanesulfonate were obtained as an oil.

A sample was crystallized from tetrahydrofuran for characterization.

m.p.: 83–85° C.

What is claimed is:

1. A process for the preparation of a salt of a 3-aminoalkanoic acid ester of formula:

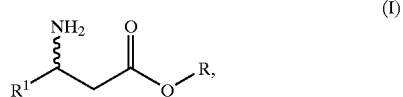

(I)

in which R is $C_{1-6}$-alkyl and $R^1$ is hydrogen, $C_{1-6}$-alkyl or phenyl, comprising: catalytically hydrogenating a corresponding 3-amino-2-alkenoic acid ester of formula:

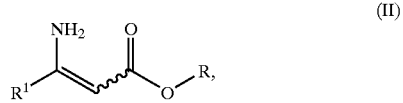

(II)

in which R and $R^1$ have the above-mentioned meanings, in the presence of a strong acid into the resultant salt of the 3-aminoalkanoic acid ester (I).

2. The process according to claim 1, wherein the strong acid employed is selected from the group consisting of hydrohalic acids, sulfuric acid, sulfonic acids and perfluoroalkanoic acids.

3. The process according to claim 2, wherein the strong acid is selected form the group consisting of hydrochloric acid, methanesulfonic acid, p-toluenesulfonic acid and trifluoroacetic acid.

4. The process according to one of claim 3, wherein the catalyst is a supported catalyst selected from the group consisting of platinum, supported catalyst, palladium supported catalysts and rhodium supported catalysts.

5. The process according to claim 4, wherein the supported catalyst is platinum on activated carbon.

6. The process according to one of claim 5, wherein R is methyl.

7. The process according to one of claim 6, wherein the hydrogenation is carried out in an anhydrous solvent.

8. The process according to claim 7, wherein the hydrogenation is carried out in the anhydrous solvent selected from the group consisting of anhydrous lower alcohols, anhydrous esters, anhydrous ethers and anhydrous haloalkanes.

9. A 3-ammonioalkanoic acid ester methanesulfonate of formula:

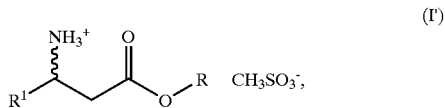

(I')

in which R is $C_{1-6}$-alkyl and $R^1$ is hydrogen, $C_{1-6}$-alkyl or phenyl.

10. Methyl (RS)-3-ammoniobutyrate methanesulfonate.

11. The process according to claim 1, wherein the catalyst is a supported catalyst selected form the group consisting of a platinum supported catalyst, palladium supported catalysts and rhodium supported catalyst.

12. The process according to claim 11, wherein the supported catalyst is platinum or activated carbon.

13. The process according to claim 1, wherein R is methyl.

14. The process according to claim 1, wherein the hydrogenation is carried out in an anhydrous solvent.

15. The process according to claim 14, wherein the hydrogenation is carried out in the anhydrous solvent selected form the group consisting of anhydrous lower alcohol, anhydrous esters, anhydrous ethers and anhydrous haloalkanes.

16. The process according to claim 1, wherein the catalyst is selected from the group consisting of platinum catalysts, palladium catalysts and rodium catalysts.

17. The process according to claim 11, wherein the catalyst support is selected from the group consisting of activated carbon, alumina, silica, silicon aluminum oxide, silicon carbide, titania, magnesia and zeolites.

18. The process according to claim 1, where the strong acid is present in equimolar amount or in small excess, based on the ester of formula (II).

19. The process for the preparation of a 3-aminoalkanoic acid ester formula:

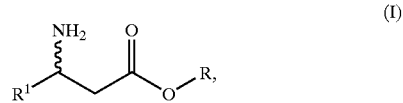

(I)

in which R is $C_{1-6}$-alkyl and $R^1$ is hydrogen, $C_{1-6}$-alkyl or phenyl, comprising: catalytically hydrogenating corresponding 3-amino-2-alkenoic acid ester of formula:

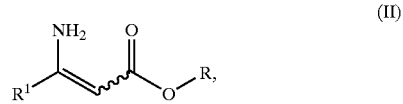

(II)

in which R and $R^1$ have the above-mentioned meanings, in the presence of a strong acid, and converting the resultant salt of the 3-aminoalkanoic acid ester (I) and the strong acid into the free 3-aminoalkanoic acid ester (I).

20. The process according to claim 19, wherein the resultant salt of the ester (I) and the strong acid is converted into the free ester (II) by addition of sodium hydroxide.

21. A process for the preparation of a salt of a 3-aminoalkanoic acid ester of formula:

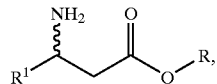

(I)

in which R is $C_{1-6}$-alkyl and $R^1$ is hydrogen, $C_{1-6}$-alkyl or phenyl, comprising: catalytically hydrogenating corresponding 3-amino-2-alkenoic acid ester of the formula:

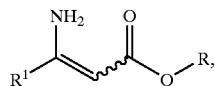

(II)

in which R and $R^1$ have the above-mentioned meanings, in the presence of a strong acid, and converting the resultant slat on the 3-aminoalkanoic acid ester (I) and the strong acid into another salt of the 3-aminoalkanoic acid ester (I).

* * * * *